(12) United States Patent  (10) Patent No.: US 9,023,009 B2
Wyss et al.  (45) Date of Patent: May 5, 2015

(54) FLEXIBLE CONTAINER WITH A PREFORMED FLUID CHANNEL AND INFUSION PUMP DEVICE USING SUCH A CONTAINER

(75) Inventors: Martin Wyss, Burgdorf (CH); Florian Kühni, Rohrbach (CH); Ulrich Haueter, Grosshöchstetten (CH)

(73) Assignee: Roche Diagnostics International AG, Rotkreuz (CH)

( * ) Notice: Subject to any disclaimer, the term of this patent is extended or adjusted under 35 U.S.C. 154(b) by 772 days.

(21) Appl. No.: 13/116,348

(22) Filed: May 26, 2011

(65) Prior Publication Data

US 2012/0136304 A1 May 31, 2012

Related U.S. Application Data

(63) Continuation of application No. PCT/EP2009/008500, filed on Nov. 30, 2009.

(30) Foreign Application Priority Data

Dec. 3, 2008 (EP) .................................... 08170627

(51) Int. Cl.
*A61B 19/00* (2006.01)
*A61M 5/148* (2006.01)
(Continued)

(52) U.S. Cl.
CPC .............. *A61M 5/148* (2013.01); *A61J 1/1475* (2013.01); *A61M 5/141* (2013.01); *A61M 5/1417* (2013.01); *A61M 5/19* (2013.01); *A61J 1/10* (2013.01); *A61M 2209/045* (2013.01)

(58) Field of Classification Search
CPC ............. A61J 1/10; A61J 1/1475; A61J 1/00; A61J 1/05; A61J 1/14; A61M 5/14; A61M 1/02; A61M 2207/00; A61M 5/148
USPC ................. 604/890.1, 85, 408–410; 222/103
See application file for complete search history.

(56) References Cited

U.S. PATENT DOCUMENTS 5,030,203 A * 7/1991 Wolf et al. ...................... 604/85
5,738,671 A * 4/1998 Niedospial et al. ........... 604/408
(Continued)

FOREIGN PATENT DOCUMENTS

EP  2 179 755 A1  4/2010
WO  2004/009162 A1  1/2004
(Continued)

OTHER PUBLICATIONS

International Search Report for PCT/EP2009/008500 dated Mar. 10, 2010.

*Primary Examiner* — Nicholas Lucchesi
*Assistant Examiner* — Diva K Chander
(74) *Attorney, Agent, or Firm* — Dinsmore & Shohl LLP (57) ABSTRACT

A flexible container for storing a liquid medicament and a device for the automated release of the liquid medicament from the flexible container are disclosed. The flexible container includes a wall and an access opening. The wall of the flexible container comprises two sheets of flexible material sealed together such that a storage volume intended to contain the liquid medicament is defined. The access opening provides a fluid connection to a conduit system in fluid connection with the storage volume via a fluid channel arranged between the storage volume and the access opening, wherein the fluid channel is formed by a cavity arranged on at least one of the two sheets.

15 Claims, 7 Drawing Sheets

(51) Int. Cl.
*A61J 1/14* (2006.01)
*A61M 5/14* (2006.01)
*A61M 5/19* (2006.01)
*A61J 1/10* (2006.01)

(56) References Cited

U.S. PATENT DOCUMENTS

| | | | |
|---|---|---|---|
| 5,779,693 A * | 7/1998 | Ropiak et al. | 604/408 |
| D407,816 S * | 4/1999 | Barney et al. | D24/118 |
| D408,533 S * | 4/1999 | Niedospial et al. | D24/118 |
| 5,911,716 A * | 6/1999 | Rake et al. | 604/890.1 |
| 5,941,866 A * | 8/1999 | Niedospial, Jr. | 604/408 |
| 5,964,738 A * | 10/1999 | Hilborne et al. | 604/249 |
| 5,984,912 A * | 11/1999 | Niedospial et al. | 604/408 |
| 6,019,751 A * | 2/2000 | Gabbard et al. | 604/408 |
| 6,179,823 B1 * | 1/2001 | Niedospial, Jr. | 604/408 |
| 6,358,239 B1 * | 3/2002 | Rake et al. | 604/890.1 |
| 7,083,068 B2 * | 8/2006 | Rake et al. | 222/103 |
| 2002/0123741 A1 * | 9/2002 | Rake et al. | 604/890.1 |
| 2004/0108333 A1 * | 6/2004 | Rake et al. | 222/103 |
| 2005/0211725 A1 * | 9/2005 | Rake et al. | 222/103 |
| 2006/0184119 A1 | 8/2006 | Remde et al. | |
| 2007/0049865 A1 * | 3/2007 | Radmer et al. | 604/93.01 |
| 2007/0123820 A1 * | 5/2007 | Gafner-Geiser et al. | 604/93.01 |
| 2008/0215029 A1 * | 9/2008 | Rake et al. | 604/408 |

FOREIGN PATENT DOCUMENTS

| | | |
|---|---|---|
| WO | 2005/081922 A2 | 9/2005 |
| WO | 2008/122135 A1 | 10/2008 |

* cited by examiner

FLEXIBLE CONTAINER WITH A PREFORMED FLUID CHANNEL AND INFUSION PUMP DEVICE USING SUCH A CONTAINER

CROSS REFERENCE TO RELATED APPLICATIONS

This application is a continuation of PCT Application PCT/EP2009/008500, filed Nov. 30, 2009, which claims priority to European Patent Application No. EP 08170627.7, filed Dec. 3, 2008.

FIELD OF THE INVENTION

The embodiments described herein relate to a flexible container for storing a liquid medicament to be administered to a patient by an infusion pump device, to a device for the automated release of a liquid medicament, and to a connection element for use with such a flexible container.

BACKGROUND

Devices for the automated release of liquid medicaments normally are used with patients who have a continuous need for a medicine that can be administered by subcutaneous infusion, which need can vary in the course of a day. Example applications for computer-controlled infusion pump devices, such as insulin pumps, include certain pain therapies and the treatment of diabetes. Such devices can be carried by a patient on the body and can contain a certain amount of liquid medicament in a medicine reservoir in the form of a container. The medicine reservoir often comprises medicine sufficient for one or several days. The liquid medicament is supplied to the patient's body from the medicine reservoir through an infusion cannula or an injection needle.

Convenience and discretion are paramount concerns for patients who may self-administer medicaments, for example, insulin, by means such as an infusion pump. Consequently, the dimensions of such infusion devices must be limited, and particularly the overall length, width and thickness should be as small as possible to prevent the devices from being evident through clothing and to allow the patient to carry the devices as comfortably as possible.

In the interest of maintaining sterility and preventing contamination, typically the devices are single-use devices. The devices may be delivered pre-filled with a certain liquid medicament, or empty, ready to be filled. This self-filling of containers has the advantage that medicaments that are not readily available in pre-filled containers can be used for such infusion pump devices, thereby providing the patient with a larger choice of sources for delivery of the medicaments. Alternatively, devices or parts of the devices can be reused by the patient, for example, by replacing an empty medicament container or by refilling the container.

Standard infusion pump devices that are carried on or near the body have a medicine reservoir with a cylindrical ampoule and a displacement piston. The piston is pushed into the ampoule by a piston rod or a threaded spindle to convey the liquid medicament. These known designs are undesirably long or thick and do not provide advantageously compact infusion pumps.

Manufacturers try to meet the demand of small infusion pump devices by various means. For example, the infusion pump can be divided into structural assemblies arranged in separate, smaller, housings that can be joined by a wireless or a wired connection. An example of such a modular infusion pump device is disclosed in US 2006/0184119 A1.

Another possibility is the use of particularly flat construction containers. For example, the cylindrical ampoule may be replaced by a container having a rectangular or other suitable cross-section and may interact with a displacement piston of a corresponding shape. Different embodiments of such compact medicine reservoir devices are shown in WO 2008/122135 A1.

A further approach to reduce the overall volume of an infusion device is to replace the syringe-type dosing mechanism with a downstream pump system. In the syringe-type dosing mechanism, an actuator displaces a piston along a long axis of a container to convey the appropriate amount of liquid medicine. In the device with a downstream pump system, a miniaturized pump downstream of the reservoir causes a suction pressure that conveys the product from the reservoir to its destination. An example of such a pump is described in WO 2004/009162 A1.

For some of the above mentioned infusion devices, the suction pressure achievable with the pump system is not very high. A suitable container for such devices is disclosed in US 2007/0123820 A1, comprising a flat container and a flat piston body arranged in the body in a sliding manner. Fully filled, such a container has a ratio of maximum height to overall width of less than 1.25. The cross-sectional area of the container in relation to the displacement axis is much larger than for conventional cylinder piston arrangements. Even a comparably small pressure gradient generated by a miniaturized pump can overcome the friction force of the piston seal as the piston glides on the inner wall of the container.

In an especially advantageous approach the rigid container and movable piston are replaced by a flexible container. Such a flexible container may comprise, for example, two flexible wall sheets that are sealed together. Flexible containers have the advantage of a smaller volume surplus of the container in relation to its content, which reduces the manufacture costs and the achievable dimensions of an infusion pump device using such a flexible container. The volume of a flexible container for use in an infusion pump device in some embodiments may be up to 10 ml, in other embodiments 5 ml or less, and in still other embodiments 1.5 to 3.5 ml.

For use in an infusion pump device the flexible container must be connected to a conduit system of the device. For that purpose the flexible container may be provided with a port. Such a port can be mounted on the container with a flange sealed to a container wall sheet. US 2007/0049865 A1 discloses such a container. The port is provided with a septum, to be punctured by a hollow needle of the conduit system of the infusion pump device. Another possibility used for flexible containers are ports in the form of flexible tubes or rigid connection pieces welded between the two sheets of the container at the periphery of the flexible container. The fastening of the port to the container, for example, by gluing or welding, requires a precise production control to avoid high rejection rates, and furthermore limits the choice of suitable materials.

A common problem of flexible containers with ports as used, for example, in IV bags, is the dead volume resulting between the collapsed container and the port. Dead volume cannot be used, meaning that it cannot be emptied. Thus, flexible containers are impossible to completely drain. The resulting loss of useable container volume due to the dead volume is particularly high for smaller containers as they are suitable for infusion pumps having a total volume of only 5 mL or less. For single-use container filled with the medicament, the dead volume considerably increases the effective costs per dose and thus of the overall therapy costs, since a certain percentage of the medicament will inevitably remain in the container and has to be disposed. This cost effect is particularly important for expensive medicaments. In addition to the increased costs, the dead volume leads also to an increase of the overall volume of the flexible container, and thus of the volume of an infusion pump device comprising such a flexible container.

A further problem, particularly of flexible containers as they are known, is air remaining in the container. If, for example, a flexible container is provided empty, intended to be filled with the appropriate medicament by the user, the dead volume initially is filled with air. However, removing the air from flexible containers as they are known from the state of the art requires a certain skill of a user. If said air remains in the container, it may be administered instead of the liquid medicament, which leads to potentially dangerous dosing errors. Furthermore, the administration of air into a patient's body should be avoided for medical reasons.

SUMMARY

Included are embodiments of a flexible container for storing a liquid medicament and a device for the automated release of the liquid medicament from the flexible container. In one embodiment, the flexible container can comprise a wall which includes two sheets of flexible material sealed together such that a storage volume intended to contain the liquid medicament is defined. The flexible container can also comprise an access opening which provides a fluid connection to a conduit system in fluid connection with the storage volume via a fluid channel arranged between the storage volume and the access opening, wherein the fluid channel is formed by a cavity arranged on at least one of the two sheets.

In a further embodiment, the flexible container for storing a liquid medicament and connectable to a conduit system of a connection element having two or more clamp parts arranged with two or more positioning bolts can comprise a wall comprising two sheets of flexible material sealed together in a sealed area such that a storage volume intended to contain the liquid medicament is defined thereby. The flexible container can also comprise an access opening which provides a fluid connection directly with the conduit system of the connection element, in fluid connection with the storage volume via a fluid channel arranged between the storage volume and the access opening, wherein the fluid channel is formed by a cavity arranged on at least one of the two sheets. The flexible container can further comprise two or more holes arranged in the sealed area which interact with the two or more positioning bolts arranged on the two or more clamp parts to lock the flexible container to the connection element such that the access opening of the flexible container remains fluidly connected to the conduit system of the connection element.

These and other features, aspects, and advantages of the present disclosure will become better understood with reference to the following description, appended claims, and accompanying drawings.

BRIEF DESCRIPTION OF THE DRAWINGS

Though the specification concludes with claims particularly pointing out and distinctly claiming the invention, it is believed that the present disclosure will be better understood from the following description taken in conjunction with the accompanying drawings of non-limiting, example embodiments, in which:

FIGS. 1A-1B schematically show an embodiment of a flexible container, wherein FIG. 1A is a perspective view, and FIG. 1B is a top view;

FIGS. 2A-2C schematically show an embodiment of a flexible container of FIG. 1A interacting with an embodiment of a connection element, wherein FIG. 2A shows a flexible container in a completely empty state, FIG. 2B shows a flexible container in a fully filled state, and FIG. 2C shows a cross-section through the connection element, perpendicular to the longitudinal axis of a flexible container;

FIGS. 3A-3B show schematic cross-sections of a further embodiment of a connection element interacting with a flexible container, wherein FIG. 3A shows the longitudinal axis of a flexible container, and FIG. 3B shows perpendicular to the longitudinal axis of a flexible container;

DETAILED DESCRIPTION

Features and advantages of the disclosure now will be described with occasional reference to specific embodiments. However, the disclosure may be embodied in different forms and should not be construed as limited to the embodiments set forth herein. Rather, these embodiments are provided so that this disclosure will be thorough and complete and will fully convey the scope of the disclosure to those skilled in the art.

One embodiment described herein provides a flexible container for storing a liquid medicament to be administered to a patient, connected to a device for the automated release of a liquid medicament to reduce dead volume, and having dimensions that are suitable for being carried on or near the body.

The flexible container according to the present disclosure is producible with high quality at low costs, and comprises a minimum number of components.

A further embodiment of the disclosure provides a connection element for connecting a flexible container with a device for the automated release of a liquid medicament.

Yet another object of the disclosure is to provide a device for the automated release of a liquid medicament comprising, incorporating, and/or capable of using a flexible container.

A flexible container for storing a liquid medicament according to an embodiment of the present disclosure comprises a wall consisting of two sheets of flexible material that are sealed together. The container comprises a storage volume which is intended to contain the liquid medicament, and an access opening in fluid connection with the storage volume. Said access opening can be fluidly connected to an infusion pump device, either directly or using a suitable connection element. In order to achieve a liquid tight connection between the access opening and the infusion pump device or the connection element, respectively, sealing elements are arranged around the access opening.

Said sealing elements and/or connection elements have to exert a certain pressure force on the access opening, in order to obtain a liquid tight connection, and as a result the two wall sheets are pressed together in a certain sealing zone around the access point. As a result the access point would be isolated from the storage volume and the fluid flow blocked. A continuous connection between the access point and the storage volume is ensured by a fluid channel that is arranged between the storage volume and the access opening. This fluid channel is formed by a cavity in one or both of the wall sheets, thus bridging the two areas on both sides of the sealing zone and ensuring a continuous fluid connection between the storage volume and the access point.

In the above embodiment another noted advantage, and not limited thereto, is the fluid channel avoids that the wall sheets, which are continuously collapsing when liquid is retrieved from the flexible container, constrict part of the storage volume from the access opening, and thereby block the fluid flow. Since the cross-section of the fluid channel is much smaller than the overall cross-section of the storage volume, having a vaulted shape, the stability of the flexible sheet material is sufficient to prevent the collapse of the fluid channel under the pressure difference generated by a pump device, even when the storage volume is completely drained.

A flexible container with such a fluid channel is the fact that no additional components have to be placed inside the container, since the fluid channel is formed in the wall sheets.

In order to minimize the dead volume and to maximize the rigidity and stability of the fluid channel, the inner diameter of the fluid channel should be as small as possible. At the same time it must be sufficiently large to allow the liquid medicament to flow through the channel. The particular minimum dimensions depend on the viscosity of the liquid, the power of the pump device, and the maximum speed with which the liquid should be drawn out of the container and into the pump device. Thus, with a fluid channel with suitable dimensions a constant and stable liquid flow from the storage volume to the access opening, and from there through the conduit system of a connection element to a downstream pump of an infusion pump device, can be provided independent of the sealing pressure force or current filling level of the flexible container. When the container is completely drained, no dead volume remains in the container except for the very small volume of the fluid channel.

The cavity forming the fluid channel may be located between an oblong corrugation or groove in one of the wall sheets and the opposite wall sheet. It is also possible that both of the wall sheets are provided with oblong corrugations or grooves oriented parallel to each other. The corrugation or groove can be produced by thermal forming or hot embossing the sheet like material of the wall, or any other suitable method for producing a cavity between two sheets. For example, a portion of a sheet may be gathered to form a pleat, prior to the laminar sealing with the second sheet, thereby forming the cavity.

In a further embodiment the container is provided with elements for positioning and/or fixating the container in a connection element of an infusion pump device. For example, two or more holes can be arranged in the sealed area of the container that may interact with corresponding elements for positioning and/or fixating of a connection element, for example, positioning bolts. Alternatively or additionally the elements for positioning and/or fixating the container may be arranged in an area of the wall which is outside of the sealed area, and which does not belong to the containment of the storage volume.

The access opening can be located at the end of the fluid channel opposite to the storage volume. In another embodiment, the access opening may be located at any position on the fluid channel, which has the advantage that liquid can flow from two or more directions to the access opening.

The access opening may most simply be a circular hole arranged in the wall sheet of the fluid channel or the wall sheet opposite to the wall sheet of the fluid channel. Such an embodiment has the advantage that no additional port is necessary for the access opening, which would have a detrimental internal dead volume. The access opening may have a diameter of about 1.5 mm or less.

A flexible container according to the present disclosure may comprise a cap or a closure element for closing the access opening. The flexible container may also be closed with a cap or closure element that has to be removed prior to first use of the container. The cap or closure can be realized as a separate entity, or comprised by a connection element. In the latter variant, the flexible container as such would be open, and all closing and/or sealing elements are comprised by the connection element.

In another embodiment, part of or all closing and/or sealing elements are part of the flexible container. For example, said elements can be mounted to the outside of one or both wall sheets, for example, by gluing or welding.

In further embodiment, the access opening is opened manually or automatically with external elements, for example, a suitable blade element or needle element. Such an element can be arranged, for example, in a connection element interacting with the container.

A container according to the present disclosure may be provided with one or more ports mounted to the container wall, in addition to the access port. These additional ports may be used for transferring liquid to and from the interior of the container, or may be used to de-aerate the container if needed. A container according to the disclosure can comprise one or more ports as disclosed in European Patent Application No. 08167548 of the applicant, which is incorporated by reference as part of this disclosure in its entirety. A container according to the disclosure can also have the structural elements of a flexible container as disclosed in said application.

A connection element according to the present disclosure for use in an infusion pump device comprises two clamp parts, which are adapted to positively and/or non-positively locking a flexible container, and fluidly connecting the access opening of the flexible container to a conduit system of the connection element. Such a conduit system is used with a flexible container according to the present disclosure.

In another embodiment of such a connection element, one or both clamp parts comprise sealing elements adapted to fluidly connect the conduit system with the access opening of the flexible container. Additionally or alternatively one or both clamp parts may also comprise resilient elements directed towards the opposite clamp part, in order to increase the friction-lock of the container element or to improve the sealing. In a further embodiment of a connection element, the surface of the clamp parts of the connection element is adapted to the exterior shape of the flexible container to be locked.

In a further embodiment the connection element comprises further functional elements, for example, a bubble filter, a degassing membrane, a pressure sensor, a pressure transfer membrane, a pump chamber and/or a pumping mechanism, complete or in part.

In yet a further embodiment, at least part of the connection element is realized as an integral part of a flexible container, permanently mounted on said flexible container.

In another embodiment according to the present disclosure, at least part of the connection element is an integral part of an infusion pump device.

A device for the automated release of a liquid medicament, for example, an infusion pump device comprises, incorporates or is capable of using a flexible container according to the present disclosure. For that purpose the infusion pump device may comprise, incorporate or be capable of using the above-mentioned connection element.

As used herein, the terms "medicament" and "liquid medicament" are meant to encompass any drug-containing flowable medicine, or therapeutic or diagnostic liquid, capable of being passed through a delivery element such as a hollow needle in a controlled manner, such as a liquid, solution, gel or fine suspension. Representative drugs include pharmaceuticals such as but not limited to peptides, proteins, and hormones, biologically derived or active agents, hormonal and gene based agents, nutritional formulas and other substances in both solid (dispensed) or liquid form. In particular the term medicament encompasses insulin preparations ready for administration.

The terms "subcutaneous infusion" and "subcutaneous injection" are meant to encompass any method in which a needle device is inserted at a selected site within the body of a patient for subcutaneous, intravenous, intramuscular, or intradermal delivery of a liquid medicament to a subject. Further, the term needle defines a piercing member (including an array of micro-needles) adapted to be introduced into or through the skin of a subject.

Referring now to the drawings, an embodiment of a flexible container according to the present disclosure is shown in FIGS. 1A-B, and FIGS. 2A-2C showing the flexible container 1 clamped in an embodiment of a connection element 5. The flexible container 1 is shown in an empty, fully drained state. The flexible container 1 comprises a wall 10, consisting of two sheets 101, 102 of flexible, liquid-tight material, sealed along a circumferential sealing rim 13. At a longitudinal end of the container 1, the sealing rim 13 merges with a sealed area 14 where a larger area of the sheets 101, 102 have been sealed together. The sealing of the sheets 101, 102 forming the wall 10 may be achieved by methods such as, for example, heat sealing, ultrasonic welding, high-frequency inductive welding, gluing, or any other suitable method for producing flexible containers from sheet-like material that is known to the skilled person. The sheet-like material may be a single foil of a suitable polymer, or a compound foil. The sealed flexible sheets define together a base area of the flexible container. The base area according to the disclosure may have any suitable shape such as, for example, that of a square, rectangular, circular, oval, or hexagonal shape. In some embodiments, the shape of the base area may be adapted to a specific infusion pump device. In some embodiments, instead of sealing together two separate sheets, the wall of the container may also be produced from a single sheet that is folded along an axis, and is sealed along the remaining edges. In further embodiments, continuous film tubes may be utilized to produce the walls of the flexible containers.

The sheet like material of the wall can be a monolayer film or a multilayer structure. The flexible container wall may comprise of one or more polymers of the following families: Polypropylene (PP), Polyethylene (PE), and copolymers; Ethylene Vinyl Acetate (EVA), Polyvinyl Chloride (PVC), Polyvinylidene Chloride (PVDC), Polystyrene (PS), Ethylene Vinyl Alcohol (EVOH), Polyethylene Terephthalate (PET), Polyamide (PA), Polychlorotrifluoroethylene (PCTFE), Cyclic Olefin Copolymer (COC), Thermoplastic Elastomer (TPE), mixtures thereof, or generally any other suitable polymer material.

The wall 10 of the flexible container may be manufactured, for example, by extrusion, blown film extrusion, coextrusion or lamination. If producing a multilayer structure, one or more tie layers may be included, or one or more adhesive layers may be applied between the functional layers. In example embodiments, metalized film, a silicon oxide or aluminum oxide coating may be applied to improve barrier properties.

Figure 1A:
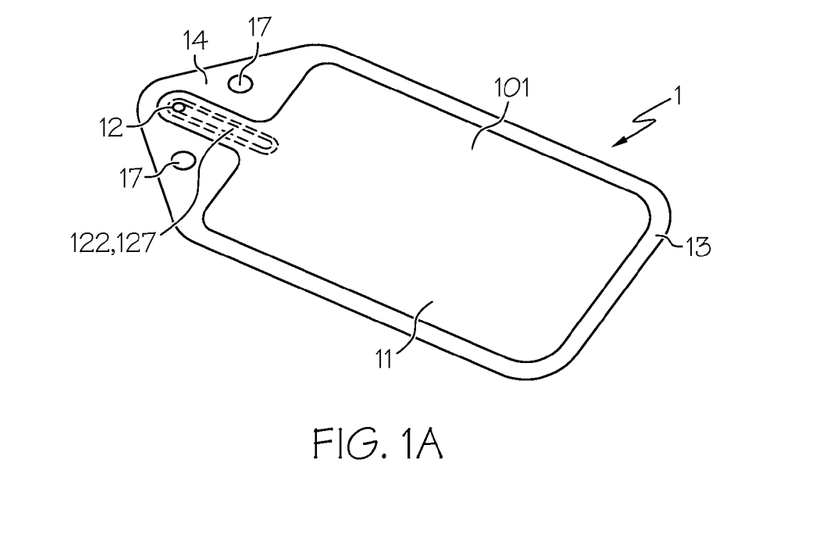
Figure 1B:
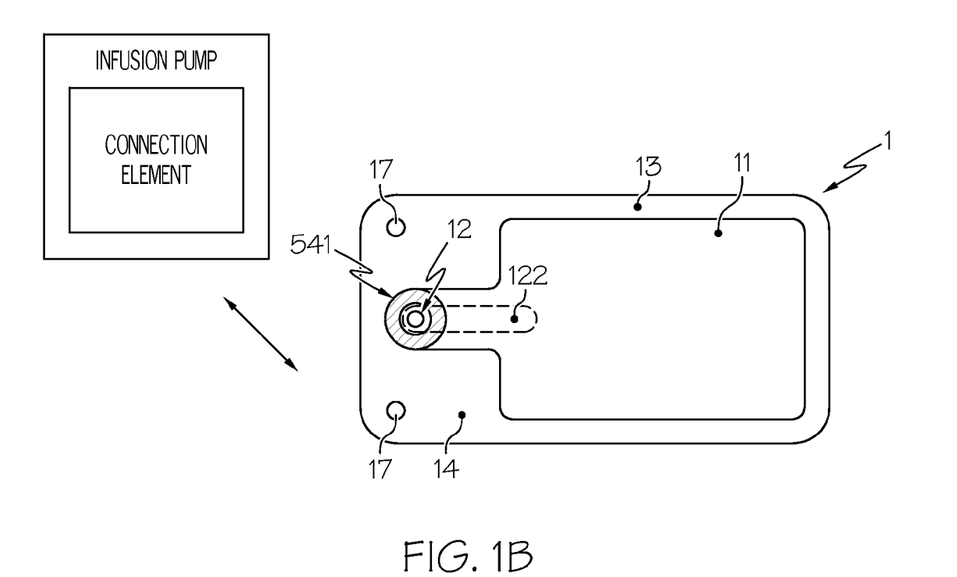

FIG. 1B shows a further embodiment of a flexible container 1 according to the present disclosure, with an essentially rectangular shape. The contact area 541 of the sealing element, sealing zone in which the sealing elements 54 are in contact with the flexible container 1 is marked in grey.

Figure 2A:
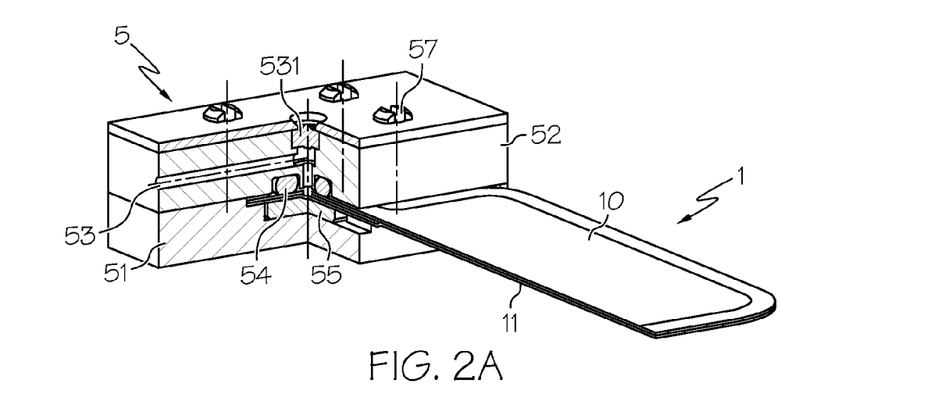
Figure 2B:
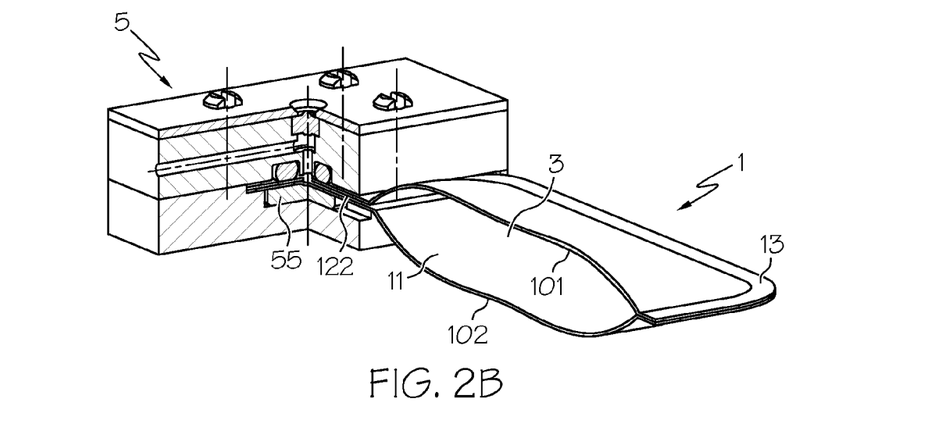
Figure 2C:
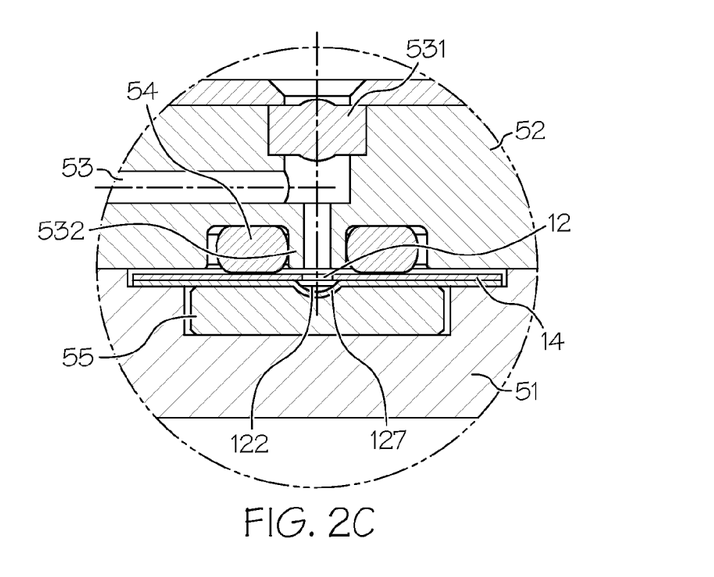

An access opening 12 located at the longitudinal end of the container 1, is in fluid connection with the storage volume 11 of the container via a fluid channel 122. Said access opening is embodied as a hole in the wall 10 at the end of the fluid channel 122 opposite to the storage volume 11, and can be connected to an infusion pump device, either directly or with a connection element 5, as shown in FIGS. 2A-2C. Because no port is necessary for the fluid connection of the container to the infusion pump device, the overall dead volume is considerably reduced.

The fluid channel 122 is embodied by an oblong cavity in the sealed area 14, located between the flat upper sheet 101 and the lower sheet 102, in which an oblong corrugation has been produced. On both sides of the fluid channel a hole 17 is arranged in the sealed area 14, which can act as an element for precisely positioning and/or fixating the container, particularly the access opening 12 in a connection element 5. Because the cross-section of the fluid channel 122 is much smaller than the cross-section of the storage volume 11, the flexible sheet material, having certain elasticity, will prevent the fluid channel from collapsing when the storage volume of the container is completely drained. The volume of the fluid channel 122 is much smaller than the total volume of the container, and thus its contribution to the dead volume of the container is negligible.

As shown in FIGS. 2A-C, the connection element 5 comprises two clamp parts 51, 52, between which a longitudinal end of the flexible container 1 can be clamped. The clamp parts may consist of any suitable stable, rigid material, such as metal or polymer. One first clamp part 51 comprises a pad 55 consisting of an elastic polymer material, arranged countersunk on the surface of the clamp part 51. The elastic pad 55 adapts its form to the protruding corrugation 127 of the fluid channel 122, respectively the wall sheet 102. Said pad 55 acts as a resilient element, since it is slightly compressed when the clamp 51, 52 is closed, and presses the access opening 12 and the adjacent wall sheet 101 against sealing elements 54 of the connection element 5. In another embodiment, the pad 55 may also have a preformed oblong groove, corresponding to the outer shape of the fluid channel.

The second clamp part 52 comprises a block with a conduit system 53, and sealing elements 54 for fluidly connecting the access opening 12 with said conduit system 53. The conduit system 53 opens out into a hollow pin 532, which is located closely above the hole of the access opening 12. An O-Ring sealing element 54 is mounted on the hollow pin 532, for a liquid-tight connection between the container and the connection element. The conduit system 53 may lead to a tube directed to a pump device, or may end in an adapter that can be connected with an infusion pump device.

In another embodiment of a connection element 5, as shown in FIGS. 2A, 2C and FIGS. 3A-B, a septum 531 is provided, for example, made from silicon polymer, arranged directly above the hollow pin 532 and the access opening 12. It should be noted that such a septum 531 is an optional feature. Through septum 531 a user may access the conduit system 53 and/or the container 1 with a syringe by penetrating the septum with a hollow needle. For example, fill or refill the container with a liquid medicament, originating from a larger container, or clean the conduit system or de-aerate the system. Furthermore, the septum 531 is for a user to puncture the sheet 101 of the wall 10 of the flexible container 1 with a needle, thereby opening the access opening 12 of a previously hermetically closed and sealed container 1.

After inserting the appropriate end of the flexible container 1 between the two clamp parts 51, 52 of the connection element 5, the two parts are locked together. A skilled person will know a number of different methods for friction-locking or form-locking said two parts. In the embodiment shown in FIG. 2A, for example, the first clamp part 51 is equipped with four snap bolts 57 (one not visible), which are inserted into corresponding holes of the second clamp part 52. Two of the snap bolts 57 also act as elements for positioning and/or fixating, interacting with the elements for positioning and/or fixating of the flexible container 1. The snap bolts 57 are inserted into the holes 17 of the container 1, thereby fixing the position in a definite way in relation to the clamp parts 51, 52.

When the pump device (not shown) of an infusion pump, arranged downstream of the conduit system 53 of the connection element 5, sucks liquid, the liquid medicament in the flexible container 1 flows from the storage volume 11 through the fluid channel 122 and the access opening 12, and then via the conduit system 53 to the pump device. The container 1, fully or partially filled in the beginning, will continuously collapse, until finally the two sheets 101, 102 abut to each other. Due to the increased structural rigidity, compared to the flexible container 1, the fluid channel 122 will not collapse, and a constant liquid flow from the storage volume 11 to the down-stream pump can be achieved, independent from the filling level of the flexible container.

Figure 3A:
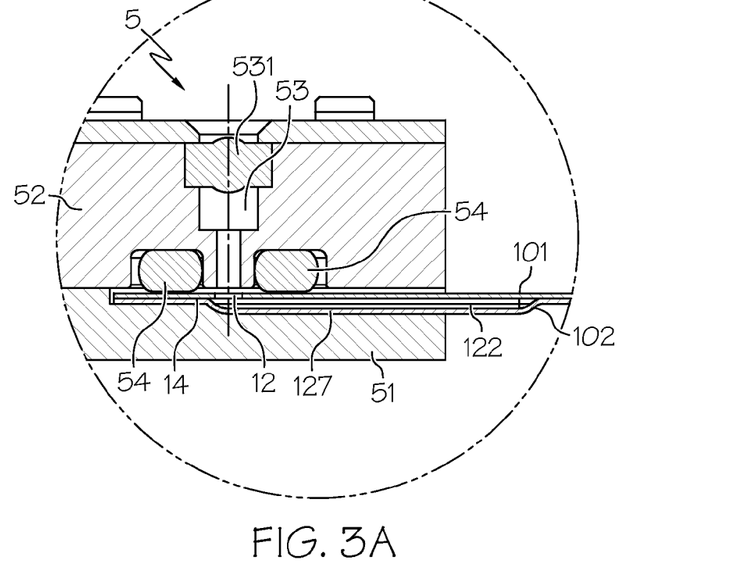
Figure 3B:
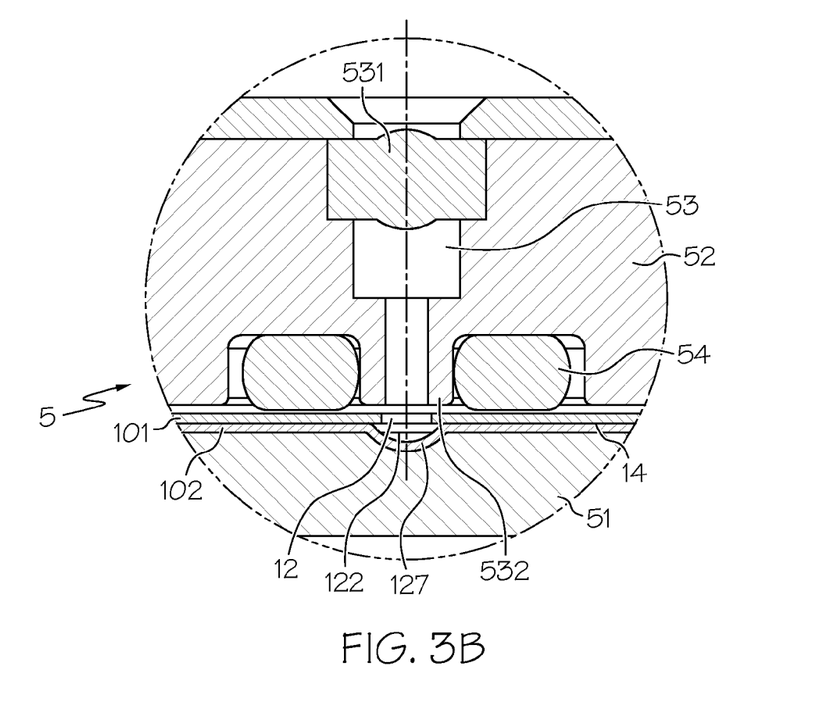

A further embodiment of a connection element 5 according to the present disclosure is shown in FIGS. 3A-B. The conduit system 53 directly ends at the septum 531, through which the conduit system 53 can be connected with the infusion pump device by a hollow needle. The lateral dimensions of the connection element 5 are chosen smaller than in FIGS. 2A-C. In the embodiment shown in FIGS. 3A-B, the first clamp part 51 does not comprise a resilient element, but a recess facing toward the container. The recess has a shape that corresponds to the fluid channel 122, thereby reducing the pressure on the fluid channel structure.

Figure 4A:
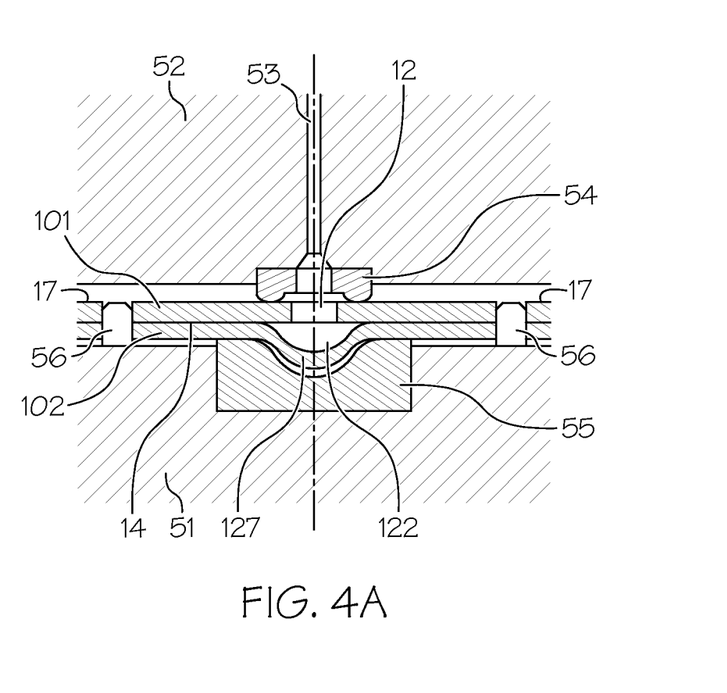
FIGS. 4A-4B show schematic cross-sections of two other embodiments of a connection element interacting with a flexible container.

A further embodiment of a connection element 5 as shown in FIG. 4A, where a conduit tube 53 is leading directly from a sealing element 54 positioned on top of the access opening 12 to the infusion pump device (not shown). A septum for accessing the container is not given. Thus this embodiment is particularly suitable for a flexible container with an additional port for accessing the container. As further shown in FIG. 4A, two positioning bolts 56 are visible, arranged on the first clamp part 51, which interact with holes 17 in the sealed area 14 of the container.

Figure 4B:
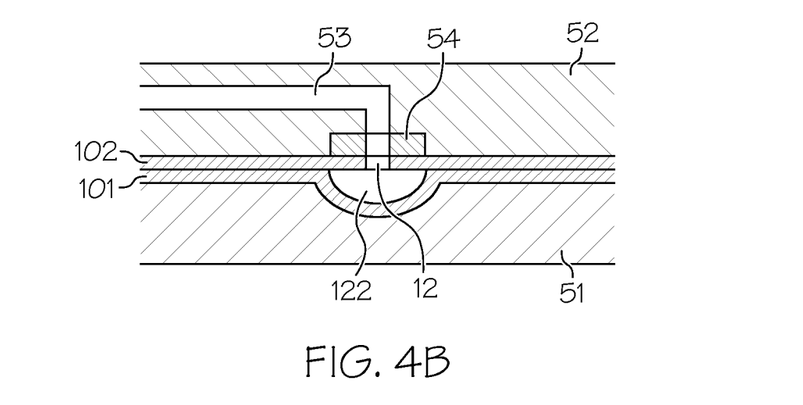

As shown in FIG. 4B, the omission of the septum allows reducing the construction height of the clamp part 52, suitable for connection elements with minimum overall height.

Figure 5A:
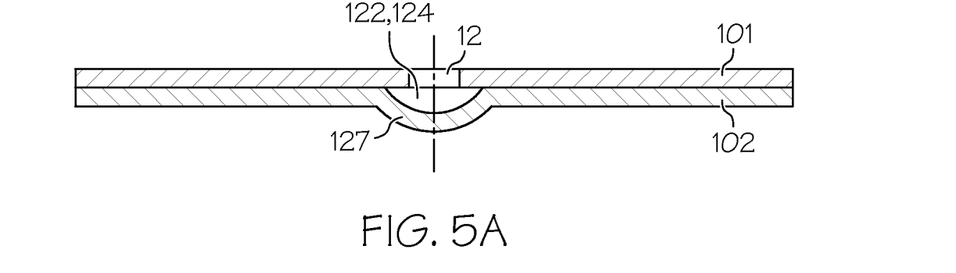
FIGS. 5A-5D schematically show four embodiments of a fluid channel in a sealed area of a wall of a flexible container.
Figure 5B:
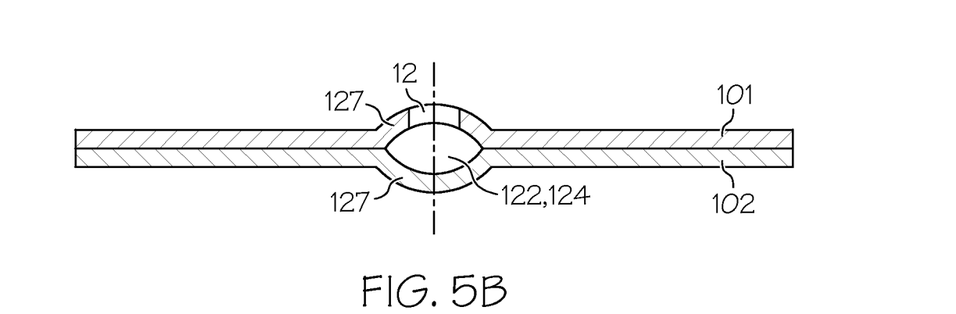
Figure 5C:
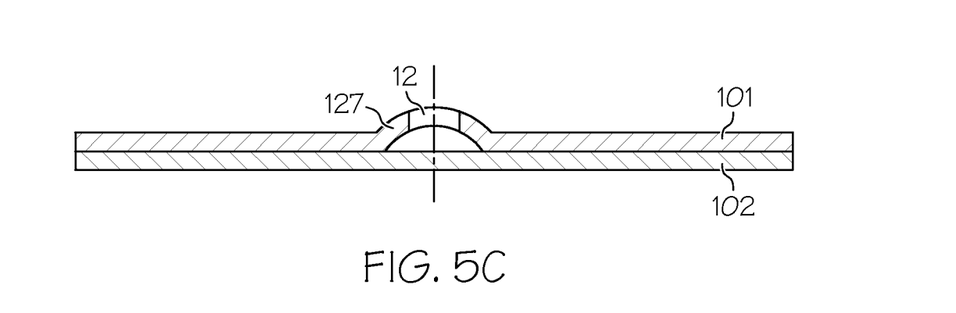
Figure 5D:
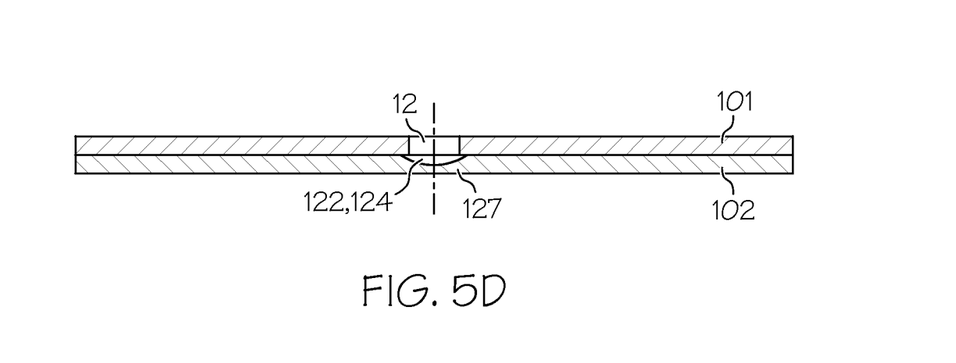

In the embodiments of flexible containers described above, the cavity 124 forming the fluid channel 122 is located between an oblong corrugation 127 in the lower sheet 102 and the other, opposite upper sheet 101 of the wall sheets as shown in FIG. 5A. However, other embodiments are possible, as is shown in FIGS. 5B-D. For example, both of the sheets 101, 102 can have oblong corrugations oriented parallel to each other, as shown in FIG. 5B. This embodiment, however, requires a precise positioning of the two sheets in relation to each other. In another embodiment, as shown in FIG. 5C, the access opening 12 is located on the corrugation 127, and not on the flat sheet.

Instead of a corrugation, one or both sheets 101, 102 may comprise a groove 127 or notch, as shown in FIG. 5D. This, however, requires a certain minimum thickness of the corresponding sheet material. Since the sealing area 14 remains flat, the clamp parts of a connection element locked to such a container can have a simpler design, because the surface of the clamp parts can be flat.

A connection element 5 according to the present disclosure may be embodied as a separate unit, as shown in FIG. 2A, or may be permanently attached to the flexible container 1, or may be directly attached to an infusion pump device. For example, the first clamp part 51 may be an integral part of a ground plate of an infusion pump device. The flexible container 1 may be easily removed from the infusion pump device, or may be an integral part of the device. A user, particularly a patient using the device, may replace an emptied container with a new, prefilled single-use container, or the user may remove the container for refilling. Replaceable single-use containers may be used for quality assurance reasons. Furthermore, the container is directly refilled in the device, for example, by a septum in the connection element or by an additional port mounted on the container. If the container has to be replaced for maintenance reasons, this may be done by the user, or by a maintenance service.

In another embodiment of a flexible container 1 according to the disclosure, the inner side of the sheets 101, 102, facing the interior storage volume 11 of the container, are equipped with drain channels. This can be achieved, for example, by hot embossing a grid of lines on at least a part of the inner surface of the wall sheet 101, particularly on one or both sheets 101, 102 of the wall. When the container collapses not ideally during emptying, no portion of the container can be blocked and separated from the fluid channel 122, even for very large containers or very flexible container wall sheets, since the liquid can always flow to the fluid channel through the grid line network on the inner side of the sheets 101, 102.

The possible geometrical form of a flexible container according to the present disclosure is not restricted to the essentially rectangular form as shown in FIGS. 1A-B and 2A-B, although a rectangular form is efficient and thus preferable. The form of the flexible container may be adapted to any specific need, particularly to the dimensions of a certain pump device. The same holds true for the form, position and dimensions of the inner storage volume and of the fluid channels, as well as the position of the access opening.

FIGS. 6A-H show, as an example, different variants of possible embodiments of flexible containers according to the disclosure. In the variants shown in FIGS. 6A-G, two essentially rectangular wall sheets are sealed together along a sealing rim 13 and sealing area 14. The form and position of the storage volume 11 is defined by the sealing rim 13 and sealing area 14. For example, in FIGS. 6A, B, F and G, the peripheral sealing rim 13 is extended toward the inner area of the wall sheets, forming a sealing area 14 that results in a specific shape of the storage volume 11.

Figure 6A:
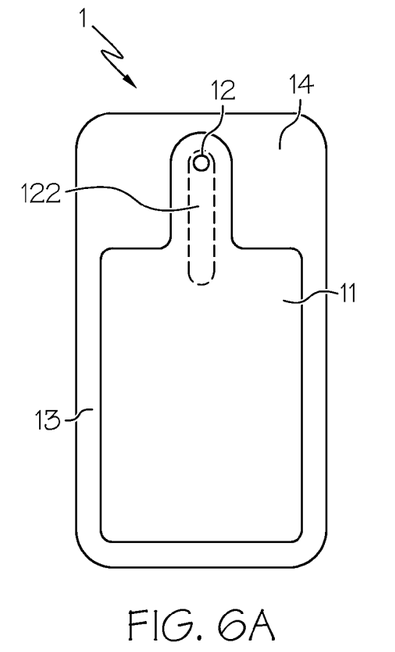
FIGS. 6A-6H show a top view of further embodiments of a flexible container.
Figure 6B:
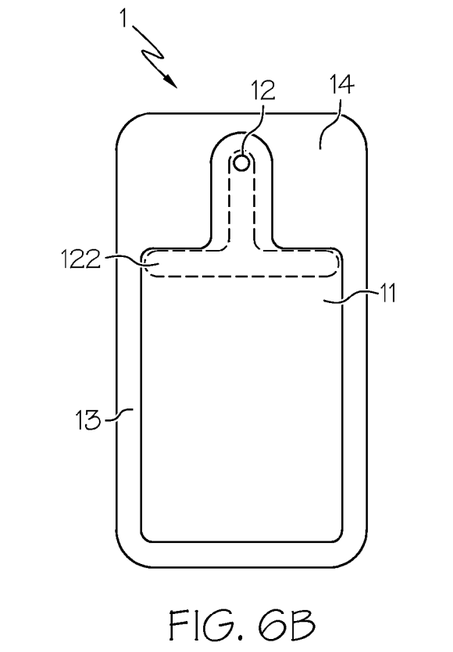
Figure 6C:
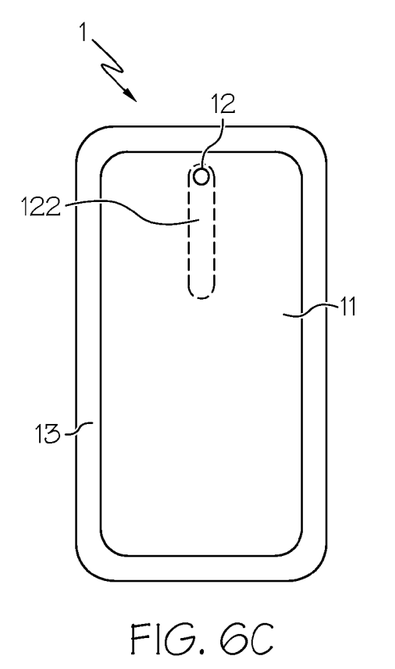
Figure 6D:
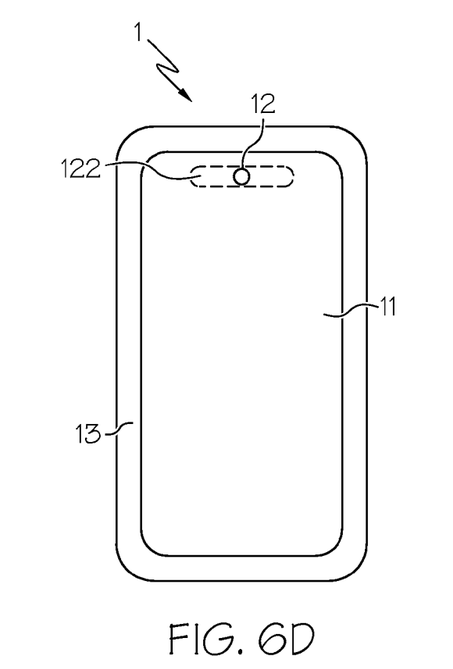
Figure 6E:
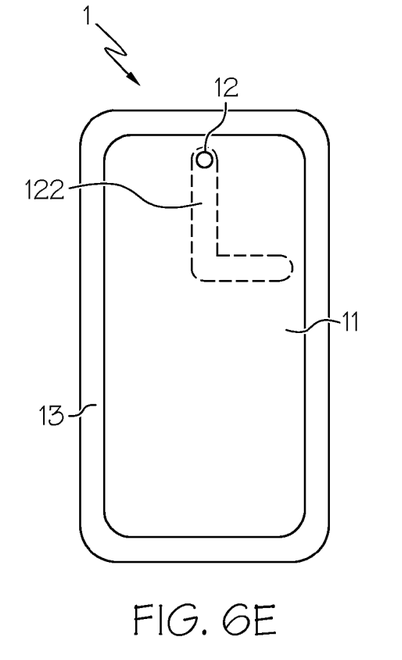
Figure 6F:
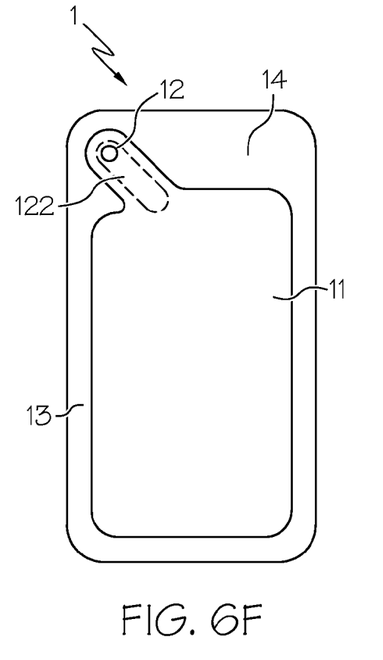
Figure 6G:
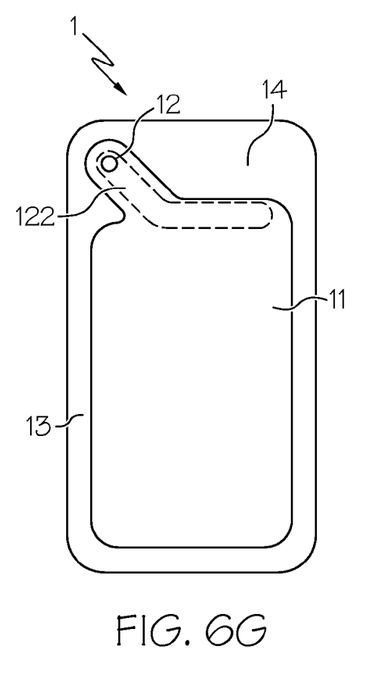
Figure 6H:
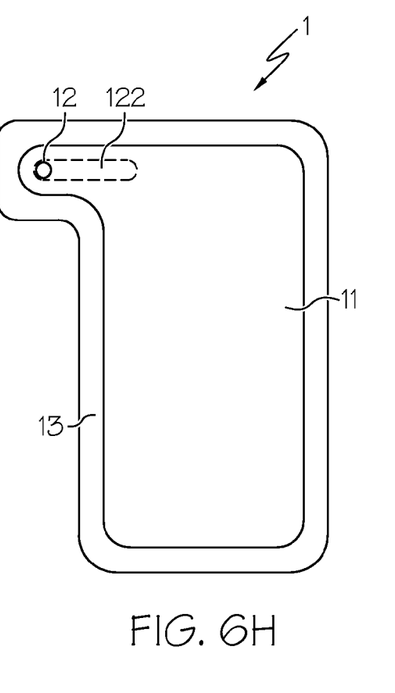

As shown in FIGS. 6A-H, the fluid channel 122 may be positioned at any suitable place inside the container 1 and may be straight, bent, or branched. The access opening 12 does not necessarily have to be located at the end of the fluid channel 122. For example, it may also be arranged in a central position of the fluid channel 122, collecting fluid from two ends of the fluid channel, as shown in FIG. 6D. The embodiments in FIGS. 6B-E and G have the advantage that the zone in which fluid can be collected from the storage volume 11 is extended. The embodiment shown in FIG. 6H has the advantage that a connection element connected with the access opening 12 can be positioned at the periphery of the flexible container, instead of being positioned on the top, which allows a flatter construction of the overall infusion pump device.

The present invention is not to be limited in scope by the specific embodiments described herein. Indeed, various modifications of the present invention, in addition to those described herein, will be apparent to those skilled in the art from the foregoing description and accompanying drawings. Thus, such modifications are intended to fall within the scope of the appended claims. Additionally, various references are cited throughout the specification, the disclosures of which are each incorporated herein by reference in their entirety.

What is claimed is:

1. A flexible container for storing a liquid medicament and use with a conduit system, the flexible container comprising:
    a wall comprising two sheets of flexible material sealed together such that a storage volume intended to contain the liquid medicament is defined; and
    an access opening, which provides a fluid connection to the conduit system in fluid connection with the storage volume via a fluid channel arranged between the storage volume and the access opening, wherein the fluid channel is formed by a cavity arranged in at least one of the two sheets such that the cavity is located between an oblong corrugation or groove formed in at least one of the two sheets; and
        elements for positioning and/or fixating the flexible container in a connection element of an infusion pump device, wherein the connection element comprises two clamp parts adapted to positively and/or non-positively lock the flexible container, and to fluidly connect the access opening to the conduit system, and at least one clamp part further comprises resilient elements directed towards the opposite clamp part of the connection element, the resilient elements comprising a pad with a preformed oblong groove, corresponding to the outer shape of the fluid channel.

2. The flexible container of claim 1, wherein the cavity is located between two oblong corrugations or grooves oriented parallel to each other in the two sheets.

3. The flexible container of claim 1, wherein the elements comprise at least two or more holes arranged in a sealed area or in an area of the wall outside of the sealed area that does not belong to the containment of the storage volume.

4. The flexible container of claim 1, wherein the access opening is a hole arranged in the wall of the fluid channel.

5. The flexible container of claim 1, further comprising at least one port mounted to the at least one of the two sheets of the wall in a peripheral sealing rim.

6. The flexible container of claim 1, further comprising closing or sealing elements mounted to the outside of at least one of the two sheets of the wall.

7. The flexible container of claim 1, wherein the at least one clamp part further comprises sealing elements adapted to fluidly connect the conduit system with the access opening.

8. The flexible container of claim 1, wherein the surface of the two clamp parts is adapted to the exterior shape of the flexible container.

9. The flexible container of claim 1, further comprising at least one positioning bolt which interacts with the elements for positioning and/or fixating the flexible container.

10. The flexible container of claim 1, wherein the connection element further comprises a septum for opening the previously closed flexible container at the access opening.

11. A device for the automated release of a liquid medicament, the device comprising at least one flexible container according to claim 1.

12. The device of claim 11, wherein the device comprises an infusion pump.

13. A flexible container for storing a liquid medicament and connectable to a conduit system of a connection element having two or more clamp parts arranged with two or more positioning bolts, the flexible container comprising:
    a wall comprising two sheets of flexible material sealed together in a sealed area such that a storage volume intended to contain the liquid medicament is defined thereby;
    an access opening, which provides a fluid connection directly with the conduit system of the connection element, in fluid connection with the storage volume via a fluid channel arranged between the storage volume and the access opening, wherein the fluid channel is formed by a cavity arranged in at least one of the two sheets such that the cavity is located between an oblong corrugation or groove formed in at least one of the two sheets; and
    two or more holes arranged in the sealed area which interact with the two or more positioning bolts arranged on the two or more clamp parts to lock the flexible container to the connection element such that the access opening of the flexible container remains fluidly connected to the conduit system of the connection element; and
    at least one of the two or more clamp parts further comprises resilient elements directed towards the opposite clamp part of the connection element, the resilient elements comprising a pad with a preformed oblong groove, corresponding to the outer shape of the fluid channel.

14. The flexible container of claim 1, wherein the access opening is arranged in the wall sheet of the fluid channel or in the wall sheet opposite to the wall sheet of the fluid channel.

15. The flexible container of claim 13, wherein the access opening is arranged in the wall sheet of the fluid channel or in the wall sheet opposite to the wall sheet of the fluid channel.

* * * * *